US006685951B2

(12) United States Patent
Cutler

(10) Patent No.: US 6,685,951 B2
(45) Date of Patent: Feb. 3, 2004

(54) ADMINISTRATION OF DIHYDROERGOTAMINE AS A SUBLINGUAL SPRAY OR AEROSOL FOR THE TREATMENT OF MIGRAINE

(75) Inventor: Neal R. Cutler, Los Angeles, CA (US)

(73) Assignee: R. T. Alamo Ventures I, Inc., Beverly Hills, CA (US)

( * ) Notice: Subject to any disclaimer, the term of this patent is extended or adjusted under 35 U.S.C. 154(b) by 0 days.

(21) Appl. No.: 10/133,120

(22) Filed: Apr. 26, 2002

(65) Prior Publication Data

US 2003/0017994 A1 Jan. 23, 2003

Related U.S. Application Data

(63) Continuation-in-part of application No. 09/899,412, filed on Jul. 5, 2001.

(51) Int. Cl.$^7$ .............................. A61K 9/00; A61F 13/00
(52) U.S. Cl. ................... 424/400; 424/422; 424/434; 424/435; 424/451; 424/484
(58) Field of Search .................. 424/400, 453, 424/451, 484, 422, 434, 435, 45

(56) References Cited

U.S. PATENT DOCUMENTS

| | | | |
|---|---|---|---|
| 4,389,393 A | 6/1983 | Schor et al. ................ 424/19 |
| 4,650,810 A | 3/1987 | Bays et al. ................ 514/415 |
| 4,914,125 A | 4/1990 | Baldinger et al. .......... 514/520 |
| 4,916,125 A | 4/1990 | Herrling et al. ............ 514/89 |
| 4,933,367 A | 6/1990 | Wolff et al. ................ 514/570 |
| 4,963,367 A | 10/1990 | Ecanow ...................... 424/485 |
| 4,994,483 A | 2/1991 | Oxford et al. .............. 514/415 |
| 5,006,342 A | 4/1991 | Cleary et al. .............. 424/445 |
| 5,021,428 A | 6/1991 | Carr et al. .................. 514/317 |
| 5,051,426 A | 9/1991 | Parnell ...................... 514/263 |
| 5,200,413 A | 4/1993 | King et al. ................. 514/299 |
| 5,242,949 A | 9/1993 | Goldberg et al. .......... 514/652 |
| 5,248,684 A | 9/1993 | Suzuki et al. .............. 514/299 |
| 5,273,759 A | 12/1993 | Simmons ..................... 424/465 |
| 5,288,498 A | 2/1994 | Stanley et al. ............. 424/440 |
| 5,317,103 A | 5/1994 | Baker et al. ................ 544/367 |
| 5,364,863 A | 11/1994 | Cohen et al. ............... 514/304 |
| 5,399,574 A | 3/1995 | Robertson et al. ......... 514/339 |
| 5,434,154 A | 7/1995 | Smith et al. ................ 514/249 |
| 5,441,969 A | 8/1995 | Axelsson et al. ........... 514/338 |
| 5,464,864 A | 11/1995 | King et al. ................. 514/468 |
| 5,466,699 A | 11/1995 | Robertson et al. .......... 514/323 |
| 5,468,768 A | 11/1995 | Cipollina et al. ........... 514/415 |
| 5,487,898 A | 1/1996 | Lu et al. ..................... 424/435 |
| 5,491,148 A | 2/1996 | Berger et al. ............... 514/305 |
| 5,494,910 A | 2/1996 | North et al. ............. 514/233.5 |
| 5,637,611 A | 6/1997 | King et al. ................. 514/468 |
| 5,672,356 A | 9/1997 | Rault et al. ................. 424/468 |
| 5,855,907 A | 1/1999 | Peyman ...................... 424/434 |
| 5,877,183 A | 3/1999 | Cincotta ..................... 514/288 |
| 5,891,885 A | 4/1999 | Caruso ....................... 514/289 |
| 5,939,425 A | 8/1999 | Caruso ....................... 514/289 |
| 5,942,251 A | 8/1999 | Merkus ...................... 424/493 |
| 5,955,502 A | 9/1999 | Hansen et al. ............. 514/558 |
| 6,010,719 A | 1/2000 | Remon et al. .............. 424/464 |
| 6,043,244 A | * 3/2000 | Caruso ....................... 514/250 |
| 6,077,539 A | 6/2000 | Plachetka et al. .......... 424/474 |
| 6,103,218 A | 8/2000 | Brucker et al. ............... 424/45 |
| 6,139,819 A | 10/2000 | Unger et al. .............. 424/9.52 |
| 6,197,331 B1 | 3/2001 | Lerner et al. .............. 424/448 |
| 6,200,604 B1 | 3/2001 | Pather et al. .............. 424/466 |
| 6,221,392 B1 | 4/2001 | Khankari et al. ........... 424/464 |

OTHER PUBLICATIONS

Goodman and Gilman's "The Pharmaceutical Basis of Therapeutics", 8th ed., McGraw–Hill, Inc. (1990), pp. 944–947.

Becker, "Migraine–associated symptoms: Clinical significance and management," Can J Clin Pharmacol 6 (Suppl A):15A–19A (1999).

Kiechel, "The Bioavailability and Kinetics of Dihydroergotamine" in Fitacha (Ed.); Neuester Scand Der Dihydergot Forschung. Stuttgart Georg Thiema: 32–46 (1984).

Migranal (dihydroergotamine mesylate, USP) Nasal Spray Information, Novartis Pharmaceuticals Company, Inc. Publication 30721901, 1997.

D.H.E. 45 (dihydroergotamine mesylate) Injection, USP Information, Novartis Pharmaceuticals Company, Inc., Publication 30220906, 1998.

* cited by examiner

Primary Examiner—Thurman K. Page
Assistant Examiner—Robert M. Joynes
(74) Attorney, Agent, or Firm—Medlen & Carroll, LLP

(57) ABSTRACT

The present invention is an improvement in the treatment of migraine headaches. By administering dihydroergotamine as a sublingual spray or aerosol, major limitations of past treatments are circumvented thereby allowing for higher efficacy and fewer side effects of treatment at lower doses.

3 Claims, No Drawings

ADMINISTRATION OF DIHYDROERGOTAMINE AS A SUBLINGUAL SPRAY OR AEROSOL FOR THE TREATMENT OF MIGRAINE

This is a continuation-in-part of application Ser. No. 09/899,412, filed Jul. 5, 2001.

FIELD OF THE INVENTION

The present invention relates to the use of dihydroergotamine for the treatment of migraine headaches via sublingual administration.

BACKGROUND OF INVENTION

Migraine is the most common neurological condition in the developed world. It affects 10% of the U.S. population and is more prevalent than diabetes, epilepsy and asthma combined. Migraine is more than just a headache. It can be a debilitating condition which has a considerable impact on the quality of life of sufferers and their families. Attacks can be completely disabling, forcing the sufferer to abandon everyday activities for up to 3 days. Even in symptom-free periods, sufferers may live in fear of the next attack. Migraine attacks normally last between 4 and 72 hours and sufferers are usually symptom free between attacks.

Migraine is believed to be caused by the release of a chemical called serotonin or 5HT into the bloodstream from its storage sites in the body, resulting in changes in the neurotransmitters and blood vessels in the brain. This causes the pain neurons in the blood vessel wall to become irritated. Exactly what cause the release of serotonin is still a subject for research and debate. However, certain factors have been identified which can trigger attacks in susceptible people. Some of these are stress or sometimes the relief of stress, lack of food or infrequent meals, foods containing monosodium glutamate, caffeine and tyramine, certain specific foods like chocolate, citrus fruits or cheese, alcohol (especially red wine), overtiredness (physical or mental), changes in sleep patterns (e.g., late nights or a weekend lie-in), or hormonal factors (e.g., monthly periods, the contraceptive pill or hormonal changes in males and females as they age), etc.

Migraine triggers are numerous and varied and occur in combinations peculiar to each individual. It should be noted that not all migraineurs will be affected by all of the above triggers and possibly by none of them. Everyone has the capacity to suffer from migraine but in some people, most probably because of a genetic predisposition, the threshold at which attacks occur is lower. Migraineurs come from all walks of life, all areas of the world and ethnic groups, and all social classes.

Migraine is a complex condition and a treatment which is successful for one patient may have no effect on another. It is therefore important to continue to develop new methods of treatment and new modes of administration of compounds that show therapeutic potential in mitigating migraines.

What is needed are compounds and drugs that are effective for the treatment of migraines in a formulation that allows for better drug delivery and ease of use by the patient.

SUMMARY OF INVENTION

The present invention relates to the use of dihydroergotamine via sublingual administration for the treatment of migraine headaches. The present invention contemplates both prophylactic and acute treatment of migraine.

Current methods of administering DHE to migraine sufferers have major efficacy limitations. For example, due to degradation in the gastrointestinal track and low adsorption of the drug, oral forms of DHE have to be administered in large doses of about 20–30 mg. These high doses may causes nausea, vomiting and other unwanted adverse side effects. Much of the DHE is subject to pre-systemic and first pass metabolism. Because of this, is it estimated that as little as 2–10% of the active unchanged drug actually reaches the blood stream. Likewise, intranasal administration of DHE is hampered with significant limitations. A 2 mg intranasal dose of a pharmaceutical salt of DHE is required and must be administered as 4 intranasal sprays with subsequent reduced systemic absorption by the unintended oral ingestion of DHE intranasal solution.

Injectable forms of DHE are also available for the treatment of migraines. Although parenteral administration of DHE into the blood stream allows for a lower dose as compared to other non-injectable methods of administration, the inconvenience of an office visit for an injection or problems with the self-administration of injectables are self evident.

Although not limited to any particular mechanism, the present invention contemplates the sublingual administration of DHE in a drug delivery system that adjusts the pH of the local environment thereby allowing for the ready absorption of DHE into the blood stream. This is because the adjustment of the pH permits the conversion of DHE to the more permeable base form. Additionally, the quick-dissolve nature of the formulation of the present invention also aids in the rapid absorption of DHE into the blood stream.

The following description does not limited the present invention to any particular mechanism and is only for illustrative purposes. 5HT agonists (sometimes known as triptans) act directly to correct the serotonin imbalance in the brain during a migraine attack. Dihydroergotamine (DHE), however, belongs to the group of medicines known as ergot alkaloids. DHE is involved in vasoconstriction (narrowing of arteries and veins that supply blood to the head). Dihydroergotamine is also involved in altering blood flow patterns that are associated with vascular headaches.

Migraine drugs are often not suitable for many patients for a variety of reasons. One of the common reasons is that the drugs are given in inconvenient or ineffective modes of administration. Often times the mode of administration may limit the effectiveness of the drug. Furthermore, some patients may have difficulty in self-administering these drugs due to the limited formulations in which they are made available.

The oral modes of administration of DHE for migraine necessitate large doses of DHE to be used, e.g., 20–30 mg for oral administration and 2 mg for nasal administration, respectively. Large doses may cause adverse side effects in the patient. For example, nausea and vomiting are common side effects. One way to reduce the severity of side effects would be to lower the dose of DHE administered to the patient while still maintaining a therapeutic level of DHE at the target site. A sublingual formulation of DHE would permit the use of lower doses of DHE since a greater portion of the medication would be absorbed directly into the blood stream thereby allowing a direct route to the afflicted target area. For example, although the present invention is not limited to any particular dose or dose range, as compared to the current marketed nasal spray formulation, the present invention contemplates about a 25% reduction in dose, giving a preferred dose in of about 1.5 mg. In another embodiment, as compared to the current marketed nasal spray formulation, the present invention contemplates about a 50% reduction in dose, giving a preferred dose of about 1.0 mg, which is the same dose as the parenteral administration. In yet another embodiment, the present invention contemplates a sublingual dose that delivers efficacy about equivalent to intranasal administration. Sublingual formulations of DHE will also allow for ease of administration by the patient. Of course, it will be clear to one practiced in the art that the dosages of DHE administered by the methods contemplated by the present invention may need to be adjusted depending on the weight, age and physical condition of the patient and use of other medications by the patient, etc.

The present invention comprises treating a patient suffering from a migraine headache with a therapeutic dose of dihydroergotamine, or a pharmacologically acceptable salt thereof, in a sublingual formulation. It is contemplated that the DHE may be in the form of dihydroergotamine mesylate or any pharmaceutically acceptable salt. It is contemplated that the sublingual administration of DHE may be made with a fast dissolve formulation.

Although the present invention is not limited to any particular mechanism, it is believed that the adjustment of the pH of the environment of the sublingual area will convert the administered DHE to the more readily absorbable DHE base. The pH of DHE in solution is typically in the range of 3.2–4.0. It is contemplated that the fast dissolve formulation comprise at least one component the will adjust the pH of the local environment of the sublingual area. The preferred pH of the sublingual environment for administration of DHE is above 4.2. The more preferred pH of the sublingual environment for the administration of DHE is between 5 and 7.

Sublingual administration of a fast dissolve DHE may take many forms. It one embodiment it is contemplated that DHE is in the form of a tablet or packed powder. The sublingual administration of DHE may comprise a medical device such as a patch. The patch may be placed under the tongue. The patch may have adhesive qualities to prevent the movement, loss or swallowing of the patch. The patch may be ingestible in case of accidental swallowing or to allow for easy disposal of the patch. In another embodiment the patch may be removed from under the tongue after the prescribed time. In yet another embodiment, the sublingual administration of DHE may take the form of a paste or gel. The paste or gel would be applied under the tongue. The viscosity of the paste or gel can be adjusted to allow for the retention under the tongue. In another embodiment, it is contemplated that the present invention is a liquid. It is further contemplated that the liquid is in the form of a spray or drops.

In one embodiment this spray will be a sublingual spray (e.g. using a nebulizer or other device). A variety of metered dose delivery devices may be adapted to the sublingual administration of a DHE spray as described in the present invention. See, U.S. Pat. Nos. 4,819,834, 5,942,251, and 6,000,580 herein incorporated by reference.

It is not intended that the present invention be limited by the concentration/amount of DHE formulated for administration as a spray or an aerosol. In one embodiment, the present invention describes a sublingual spray containing DHE at 4 mg/ml in an aqueous solution that will be formulated as a stable pharmaceutical composition. In another embodiment the present invention describes a sublingual spray containing DHE at 5.0 mg/ml. In another embodiment the present invention describes a sublingual spray containing DHE at 2.5 mg/ml. Specifically, such a stable pharmaceutical composition will contain: 1) DHE and/or a salt of DHE (mesylate or tartrate) and 2) cyclodextrin and/or other saccharides and/or sugar alcohols.

The present invention also contemplates the administration of a sublingual spray that will be formulated as a liquid or sol-gel. The compounds of the present invention may also be aerosolized.

Sublingual powder formulations (suitable for administration as an aerosol) may be made by mixing crystallized DHE and a solid excipient (both having a desired particle size). Other methods for the production of a powder formulation include making a solution of DHE and cyclodextrin followed by precipitation, filtration and pulverization of the precipitated solid. It is also possible to remove the solvent by freeze drying, followed by pulverization of the powder into a desired particle size. This pulverization is followed by size classification, by sieving in one embodiment, to capture particles that are less than 100 microns in diameter and, more preferably, between 50 and 100 microns in diameter. These powder formulation may administered as a substantially dry powder in an aerosol or as a suspension in liquid organic fluids which are then sprayed.

While it is not intended that the present invention be limited by any dosage volume, the volume of (liquid or sol-gel) DHE administered as a sublingual spray will be between approximately 0.01 ml and 1.0 ml. In another embodiment, the volume of (liquid or sol-gel) DHE administered as a sublingual spray will be between approximately 0.1 ml and 0.4 ml. The amount of a powder sublingual DHE formulation (e.g. not a solution, but rather, a largely dry preparation) will be approximately between 1 and 15 mg.

Specific liquid, sol-gel, and powder formulations are described in the "Experimental" section of the instant application.

In a particularly preferred formulation in accordance with the present invention there is provided a hard, compressed, rapidly dissolving tablet adapted for direct sublingual dosing. The tablet includes particles made of an active ingredient and a protective material. These particles are provided in an amount of between about 0.01 and about 75% by weight based on the weight of the tablet. The tablet may also include a matrix made from a nondirect compression filler, a wicking agent, and a hydrophobic lubricant. The preferred tablet matrix comprises at least about 60% rapidly water-soluble ingredients based on the total weight of the matrix material. The preferred tablet has a hardness of between about 15 and about 50 Newtons, a friability of less than 2% when measured by U.S.P. and is adapted to dissolve spontaneously in the mouth of a patient in less than about 60 seconds (and, more preferably, less than about 30 seconds) and thereby liberate said particles and be capable of being stored in bulk.

In yet another preferred formulation the compressed rapidly dissolving tablet comprises effervescent agents. These effervescent agents allow enhanced adsorption of the active ingredient across the mucosal membranes in the sublingual cavity. An example of effervescent pharmaceutical compositions suitable for use in conjunction with the present invention are the compositions described in Pather, U.S. Pat. No. 6,200,604, which is incorporated herein by reference.

In one embodiment of the present invention, it is contemplated that DHE is combined with inactive ingredients. Such ingredients may be necessary, e.g., to add bulk to the pharmaceutical preparation, to bind the preparation, to add color or flavor to the preparation, to prevent degradation or growth of contaminants, etc.

It is also contemplated that the present invention comprise other active ingredients in addition to DHE which may be added to the pharmaceutical preparation of the present invention. The addition of any other active ingredient or ingredients is contemplated except where limited by the prior art. Such added active ingredients may augment the effectiveness of DHE in alleviating or ameliorating migraines. For example, it is contemplated that analgesics or anesthetics may be added to the pharmaceutical preparation. In a particular embodiment, non-steroidal anti-inflammatory drugs (NSAID) are contemplated as additional active ingredients. The present invention is not limited to any particular type of NSAID. In another embodiment, the present invention contemplates the addition of active ingredients that may help to alleviate any side effects of the medication or of the migraine. In one embodiment the added agent may alleviate nausea and vomiting. It is contemplated that the other active ingredients be administered in combination with the sublingual dose of DHE. Such co-administration may be sublingual, oral, rectal, buccal, injectable, nasal, transcutaneous, etc.

In yet another embodiment, the present invention contemplates that the sublingual composition of DHE comprises a solid preparation comprising granules wherein each comprises a fine particulate core and a drug layer coated on said fine particulate core, said drug layer comprising (1) an base and (2) a pH-dependent or pH-independent drug and said drug occurring as a solid solution in said base as disclosed in U.S. Pat. No. 5,624,687 to Yana, et al., which is herein incorporated by reference.

In yet another embodiment of the present invention, it is contemplated that the sublingual composition comprises an ordered mixture of one or more bioadhesive and/or mucoadhesive carrier substances coated with the pharmaceutically active agent or agents in a fine particulate form, as disclosed in PCT application WO 00/16750, which is incorporated herein by reference.

In one embodiment, it is preferred to formulate the composition according to the invention by use of the technology for formulating rapidly dissolving ordered-mixture compositions disclosed in European patent EP 0 324 725. In these compositions, the drug in a finely dispersed state covers the surface of substantially larger carrier particles. Such compositions disintegrate rapidly in water, thereby dispersing their contents of microscopic drug particles.

It was therefore unexpected that the present form of a solid dosage form preparation and administration route gives positive and useful results. In such an ordered mixture, the active agent or agents have a mean particle size below, for example, about 10 $\mu$m. This size is determined on a weight basis, as obtained directly by, e.g., dry sieving analysis, as is known by those skilled in the art.

In another embodiment, a bioadhesion and/or mucoadhesion promoting agent is additionally added to the carrier particles according to the invention. The bioadhesion and/or mucoadhesion promoting agent is effective in making the active agent or agents adhere to the oral mucosa and may, in addition, possess properties to swell and expand in contact with water and thus make the tablet or the carrier particles disintegrate when wetted with saliva. The bio/mucoadhesion promoting agent must then be present on the surface of the carrier particles, but it may optionally also be present within these particles, as described below.

It is contemplated that the carrier particles contain, for example, from about 0.1 up to 25 weight percent of bio/mucoadhesion promoting compound, based on the total composition. The preferred range of bio/mucoadhesion promoting agent content is from about 1.0 to 15.0 weight percent.

In a preferred embodiment, the bio/mucoadhesion promoting agent is a polymeric substance, preferably a substance with an average molecular weight above 5,000 (weight average). Although the present invention is not limited to any particular mechanism, it is believed that the level of hydration of the mucosa adhesion promoting agent interface is of importance in the development of bio/mucoadhesive forces. Therefore, the faster the swelling of the polymer, the faster is the initiation of bio/mucoadhesion. Additionally, it is contemplated that the hydration of bioadhesive compounds also makes them useful as absorption enhancers according to the invention.

In one embodiment, it is contemplated that the carrier particle size is, for example, from about 50 to 750 $\mu$m and, preferably, from about 100 to 600 $\mu$m. The carrier used may comprise any substance which is pharmaceutically acceptable, is highly soluble in water, and which can be formulated into particles fit for incorporating a bio/mucoadhesion promoting agent. A number of such substances are known to the person skilled in this art. For example, sugar, mannitol and lactose, or pharmaceutically acceptable inorganic salts, such as sodium chloride or calcium phosphate may be used.

In another embodiment, it is contemplated that the carrier also comprises a fragmentation promoting agent. A fragmentation promoting agent is a brittle material which is readily crushed or broken up when a pharmaceutical composition of which it forms a part is compacted into tablets. For example, and without limiting the present invention to any particular theory, if a bio/mucoadhesion promoting agent also is incorporated within the carrier as well as being added to the carrier surface, further surfaces of bio/mucoadhesion promoting agent may then be exposed for hydration. This effect is especially pronounced when the bio/mucoadhesion promoting agent also serves as a disintegrant. As examples, mannitol and lactose have been found to be particularly suitable as fragmentation promoting agents.

In another embodiment, it is contemplated that a pharmaceutically acceptable surfactant is added to the composition. Although the present invention is not limited to any particular mechanism, it is believed that the increased wetting effect of the surfactant enhances the hydration of the carrier particles, which results in faster initiation of the bio/mucoadhesion. In one embodiment, the surfactant is in a finely dispersed form and well mixed with the active agent or agents. The amount of surfactant should be, for example, from about 0.5 to 5.0 weight percent of the composition, and preferably from about 0.5 to 3.0 weight percent. As examples of suitable surfactants may be mentioned sodium lauryl sulfate, polysorbates, bile acid salts and mixtures of these.

In another embodiment, it is contemplated that a variety of polymers known in the art can be used as bio/mucoadhesion promoting agents. An example of a contemplated polymer is one that is swellable while also being substantially insoluble in water. In one embodiment, the swelling factor by volume when brought into contact with water or saliva should preferably be, for example, at least 10 to 20. Examples of such bio/mucoadhesion promoting agents include cellulose derivatives such as hydroxypropylmethyl cellulose (HPMC), hydroxyethyl cellulose (HEC), hydroxypropyl cellulose (HPC), methyl cellulose, ethyl hydroxyethyl cellulose, carboxymethyl cellulose and sodium carboxymethyl cellulose (NaCMC); starch derivatives such as moderately cross-linked starch, acrylic polymers such as carbomer and its derivatives (Polycarbophyl, CarbopolQ etc.); polyethylene oxide (PEO); chitosan (poly-(D-glucosamine)); natural polymers such as gelatin, sodium alginate, pectin; scleroglucan; xanthan gum; guar gum; poly co-(methylvinyl ether/maleic anhydride); microcrystalline cellulose (Avicela); and crosscaramellose. It is also contemplated that combinations of two or more bio/mucoadhesive polymers be used. More generally, any physiologically acceptable agent showing bio/mucoadhesive characteristics may be used successfully to be incorporated in the carrier. Bio/mucoadhesiveness can be determined in vitro, e.g., according to G. Sala, et al., (Proceed. Int. Symp. Contr. Release. Bioact. Mat. 16:420, 1989), which is incorporated herein by reference.

Some suitable commercial sources for representative bio/mucoadhesive polymers include:

Carbopol@ acrylic copolymer—BF Goodrich Chemical Co, Cleveland, 08, USA;
HPMC—Dow Chemical Co., Midland,), Mich., USA;
NEC (Natrosol)—Hercules Inc., Wilmington, Del., USA;
25 HPC (KlucelB)—Dow Chemical Co., Midland, Mich., USA;
NaCMC—Hercules Inc. Wilmington, Del. USA;
PEO—Aldrich Chemicals, USA;
Sodium Alginate,—Edward Mandell Co., Inc., Carmel, N.Y., USA;
Pectin—BF Goodrich Chemical Co., Cleveland, Ohio, USA;
30 Ac-Di-Sol@ (modified cellulose gum with a high swellability)—FMC Corp., USA;
Actigum,—Mero-Rousselot-Satia, Baupte, France;
Satiaxane—Sanofi BioIndustries, Paris, France;
GantrezB—ISP, Milan, Italy;
Chitosan—Sigma, St Louis, Miss., USA.

Depending on the type and the proportion of the bio/mucoadhesion promoting agent used, the rate and intensity of bio/mucoadhesion may be varied. According to one embodiment of the invention, substances with high and rapid capacity for swelling are preferred.

Although the present invention is not limited to any particular method of production, it is contemplated that the bio/mucoadhesion promoting agent should be positioned at the surfaces of the carrier particles. The bio/mucoadhesion promoting agent can be admixed to the carrier particles in several ways. In a preferred embodiment of the invention, a fine particulate quality of the bio/mucoadhesion promoting agent is mixed together with the coarse carrier for a sufficient time to produce an ordered mixture, where the bio/mucoadhesion promoting agent particles exist as discrete primary particles adhered to the surfaces of the carrier particles. Thus, in one embodiment, the bio/mucoadhesion promoting agent is admixed in the same way as the active compound described in European Patent No. 0 324 725, which is incorporated herein by reference.

In yet another embodiment of the invention, the bio/mucoadhesion promoting agent may, besides being positioned in peripheral orientation on the surfaces of the carrier particles, also be incorporated into the carrier particles in various ways. For example, it is contemplated that the finely dispersed carrier can be granulated together with a finely dispersed bio/mucoadhesive agent in a liquid which does not dissolve the bio/mucoadhesive agent or cause it to swell. In this case, the dry constituents are fast mixed, and the resultant mix is then moistened with a non-dissolving/non-swelling liquid, such as absolute ethanol. The resultant mass is granulated, for example, by forcing it through a filter. It is then dried and finely ground. Alternatively, it is also contemplated that the moist mass can he dried and then granulated. Another way of producing the carrier particles is contemplated by dissolving the carrier agent in a solvent which will not dissolve the bio/mucoadhesion promoting agent or cause it to swell, followed by the addition or the bio/mucoadhesion promoting agent to the solution, evaporation of the solvent, and granulation of the residue. Other methods are also conceivable to the person skilled in this art. Irrespective of the method applied, a suitable grain size fraction of the carrier agent containing bio/mucoadhesion promoting agent is prepared in a final stage, e.g., by passing the particulate mixtures through an screen or sieve of an appropriate mesh size, for instance a U.S. mesh size from about 35 to 170.

The bio/mucoadhesion promoting agent has a particle size between about 1 $\mu$m and about 100 $\mu$m. When the particles of this agent are mixed with the carrier particles to form an ordered mixture, their size falls within the lower part of the size interval, and suitably their size is then below 10 $\mu$m. When the bio/mucoadhesion promoting agent is to be incorporated in the carrier particles, its particle size may be within the upper part of the size interval.

In one embodiment, the present invention contemplates a method of treating migraines, comprising: a) providing i) a patient having one or more symptoms of a migraine and ii) a formulation comprising dihydroergotamine; b) administering said formulation to said patient sublingually under conditions such that said one or more symptoms of said migraine are reduced. In another embodiment, the DHE is a pharmaceutically accepted salt. In yet another embodiment, DHE is a pharmaceutically accepted base. In yet still another embodiment, the administration is sublingual administration is via a liquid. In yet still another embodiment, the is liquid is administered by a spray. In yet still another embodiment, the liquid is administered by drop. In yet still another embodiment, the sublingual administration is via a paste or gel. In yet still another embodiment, the sublingual administration is via a tablet or compressed powder. In yet still another embodiment, the method additionally comprises the co-administration of at least one other pharmaceutically accepted compound. In yet still another embodiment, the pharmaceutically accepted compound is a non-vasodilating treatment for migraine. In yet still another embodiment, the therapeutic formulation of DHE additionally comprises a pain reliever. In yet still another embodiment, the therapeutic formulation of DHE additionally comprises an anti-emetic. In yet still another embodiment, the said sublingual administration is via a fast dissolve formulation. In yet still another embodiment, the formulation additionally comprises at least one effervescent agent. In yet still another embodiment, the formulation additionally comprises at least one pH adjusting agent.

In one embodiment, the present invention contemplates a method of treating migraines, comprising: a) providing i) a patient having one or more symptoms of a migraine and ii) a formulation comprising dihydroergotamine; b) administering said formulation to said patient sublingually under conditions such that said one or more symptoms of said migraine are reduced. In another embodiment, the formulation additionally comprises at least one bio/mucoadhesion agent. In yet another embodiment, the formulation comprising at least one bio/mucoadhesive agent additionally comprises at least one disintegrant. In yet still another embodiment, the formulation comprising at least one disintegrant additionally comprises at least one pain reliever and/or antiemetic. In yet still another embodiment, the sublingual administration is via a fast dissolve formulation.

In one embodiment, the present invention contemplates a method of treating migraines, comprising: a) providing i) a patient having one or more symptoms of a migraine and ii) a formulation comprising dihydroergotamine; b) administering said formulation to said patient sublingually under conditions such that said one or more symptoms of said migraine are reduced. In another embodiment, the present invention contemplates In another embodiment, said dihydroergotamine is a pharmaceutically accepted salt. In yet another embodiment, said dihydroergotamine is a pharmaceutically accepted base. In yet still another embodiment, said sublingual administration is via a liquid. In still yet another embodiment, said liquid is administered by a spray. In still yet another embodiment, said liquid is administered by drop. In still yet another embodiment, said sublingual administration is via a paste or gel. In still yet another embodiment, said sublingual administration is via a tablet or compressed powder. In still yet another embodiment, said method additionally comprises the co-administration of at least one other pharmaceutically accepted compound. In still yet another embodiment, said pharmaceutically accepted compound is a non-vasodilating treatment for migraine. In still yet another embodiment, said therapeutic formulation of DHE additionally comprises at least one pain reliever. In still yet another embodiment, said therapeutic formulation of DHE additionally comprises at least one antiemetic. In still yet another embodiment, said sublingual administration is via a fast dissolve formulation. In still yet another embodiment, said formulation additionally comprises at least one effervescent agent. In still yet another embodiment, said formulation additionally comprises at least one pH adjusting agent. In still yet another embodiment, said formulation additionally comprises at least one bio/mucoadhesion agent. In still yet another embodiment, said formulation additionally comprises at least one disintegrant.

In one embodiment, the present invention describes a method of treating migraine comprising: the application of a spray to the sublingual mucosa of a patient wherein said spray comprises dihydroergotamine and an ingredient selected from the group consisting of cyclodextrins, dextrans, sugar alcohols and mixtures thereof. In another embodiment, theses dextrans have average molecular weight between about 10,000 and about 100,000.

In one embodiment the present invention describes a method of treating migraine comprising: the application of an aerosol to the sublingual mucosa of a patient wherein said aerosol comprises dihydroergotamine and an ingredient selected from the group consisting of cyclodextrins, dextrans, sugar alcohols and mixtures thereof.

Definitions

"Migraine" and "migraine headache" is defined herein as a recurrent, throbbing headache generally, but not always, felt on one side of the head.

"Sublingual" is defined herein as beneath or concerning the area under the tongue.

"Sublingual administration" is defined herein as the therapeutic administration of a pharmaceutical composition under the tongue. Such pharmaceutical compositions may be formulated so that they dissolve when placed under the tongue. The pharmaceutical compositions may dissolve slowly, moderately quickly or rapidly. Additionally, such sublingual formulations may constitute a medical device that comprises the therapeutic compound and is removed from under the tongue and taken out of the mouth once the compound has been released dissolved or after a prescribed amount of time.

"Oral administration" is defined as a mode of administration of a pharmaceutical in which the pharmaceutical compound is administered by mouth and swallowed.

"Dihydroergotamine," "DHE," "dihydroergotamine mesylate" and synonyms thereof, shall be defined as a therapeutic amount of dihydroergotamine or a pharmaceutical acceptable derivative or salt thereof.

"Migraine-ameliorating effective amount" shall be defined as an amount of dihydroergotamine which effects a prophylactic or therapeutic response in the patient in need of such a response over a reasonable time frame (e.g., between 0.5 and 2.5 hours), causing either a diminution or an eradication of one or more of the symptoms of migraine (e.g., a reduction in throbbing or pain). A migraine-ameliorating effective amount may be a dose that gives equivalent efficacy as an intranasal administered dose of DHE.

"Analgesic" shall be defined as a chemical substance capable of causing diminished sensitivity to pain.

"Antiemetic" shall be defined as a chemical substance capable of causing diminished nausea and or vomiting.

"Vasoconstrictor" shall be defined as a chemical substance that induces the narrowing of the lumen of blood vessels, i.e., vasoconstriction. "Non-vasodilating" shall be defined as a compound, drug, pharmaceutical, treatment or therapy that does not induce vasoconstriction.

"Therapeutic formulation" shall be described as a pharmaceutical composition comprising at least one active ingredient along with other optional ingredients useful in, for example, binding, flavoring, coloring, preserving, stabilizing, increasing self life, adding structural rigidity, adding desired mouth feel, adding desired mouth consistency, aiding in regulating dissolution rate, adjusting the pH of the local environment or adding adhesive qualities to promote absorption into the systemic circulation.

"Water-soluble" in accordance with the present invention has its usual meaning. However, "rapidly water-soluble" shall be defined as the ingredient in question will dissolve in a time frame as defined below under "fast dissolve". For example, a very fine grained or powdered sugar known as a nondirect compression sugar may be used as a filler in the matrix of the present invention. This material, in part because of its chemical composition and in part because of its fine particle size, will dissolve readily in the mouth in a mater of seconds once it is wetted by saliva.

"Dosage form," in accordance with the present invention, includes tablets, solutions, pastes, gels, patches and "slugged cores" used in capsules or caplets (a hybrid tablet/capsule).

"Dissolvable," shall be defined as describing the action of the dosage form as it is held in the mouth. In this case, the dosage form gets continuously smaller in a process which is conceptually analogous to melting. While the dosage form may also disintegrate into smaller pieces to some extent, particularly where a relatively greater amount of a wicking agent or effervescent disintegrant is used, that is not its principal mechanism.

"Rapidly dissolve(able)", "rapid(ly) dissolving" and "fast dissolve(able)" shall be defined as the rapidly water-soluble ingredients will dissolve sufficiently to allow at least 50% solubilization of the active ingredient or ingredients in (120 seconds or less, preferably 60 seconds or less and most preferably 30 seconds or less.

"Effervescent agent" shall be defined as compounds that evolve gas. The preferred effervescent agents evolve gas by means of a chemical reaction that takes place upon exposure of the effervescent agent to an aqueous solution such as water or saliva.

"Administered in combination", "co-administered" or equivalent terms, shall be defined as pharmaceuticals that are administered simultaneously or sequentially with DHE. The pharmaceuticals administered need not be in the same dosage form (i.e., sublingual) as the DHE. "In combination with" DHE shall be defined as the administration of the other drug either simultaneously or sequentially with DHE.

"pH adjusting agent" shall be defined as a compound that, alters or adjusts the pH of the local environment. In the context of the present invention, a "pH adjusting agent" alters or adjusts the pH of the sublingual area upon dissolving. The pH of DHE in solution is typically in the range of 3.2–4.0. It is contemplated that the fast dissolve formulation of the present invention comprise at least one component the will adjust the pH of the local environment of the sublingual area. The preferred pH of the sublingual environment for administration of DHE is above 4.2. The more preferred pH of the sublingual environment for the administration of DHE is between 5 and 7.

"Reduced" and "reduced symptoms" shall be defined as a lessening of symptoms to a noticeable degree by either the patient or medical professional. In the context of the present invention reduced symptoms shall mean, for example, the lessened severity of the subject's migraine headache. "Lessened severity" shall be defined, for example, as reduced pain, reduced throbbing, an increased ability for the subject to perform his or her normal routine, etc. It is not necessary, in the context of the present invention, for the treatment to relieve all symptoms of the migraine or to completely relieve the symptoms of the migraine.

The expressions "mucoadhesion", "bioadhesion" and "bio/mucoadhesion" generally overlap as definitions, may usually be used interchangeably and are meant to denote an adhesion to a biological or mucosal surface. Additionally, a "bio/mucoadhesive promoting agent" is a substance that aids in the adhesion of a compound to a biological or mucosal surface.

"Ordered mixture" shall be defined as, and synonymous with, a homogeneous mixture. In the context of the present invention, a homogeneous mixture is a mixture in which the constituents are evenly dispersed or nearly evenly dispersed (e.g., 90% dispersed).

"Disintegrant" shall be defined as a component of a solid formulation that acts as a agent that promotes the fragmentation or breakdown of the formulation. Mannitol and lactose examples of disintegrants that are used in an embodiment of the present invention. These agents work by, for example, becoming moist in the sublingual cavity and dissolving thereby resulting in the disintegration or breakdown of the solid formulation.

"Patient" shall be defined as a person having symptoms of migraine headaches.

As used herein, "cyclodextrins" refers to cyclic oligosaccharides (like alpha-, beta- and gamma-cyclodextrin and their derivatives, preferably beta-cyclodextrin and its derivatives, preferably methylated beta-cyclodextrin) with a degree of CH3-substitution between 0.5 and 3.0, more preferably between 1.7 and 2.1.

As used herein, "saccharides" refers to disaccharides, like lactose, maltose, saccharose and also refers to polysaccharides, like dextrans, with an average molecular weight between 10.000 and 100.000, preferably 40.000 and 70.000.

As used herein, the term "sugar alcohols" refers to mannitol and sorbitol.

As used herein, the term "spray" refers to a liquid minutely divided or nebulised as by a jet of gas(es).

As used herein, the terms "aerosol" or "aerosolized" refer to a gaseous suspension of fine solid or liquid particles.

As used herein, the term "sol-gel" refers to a colloidal suspension which may transition from a liquid (sol) to a more solid material (gel).

GENERAL DESCRIPTION OF INVENTION

The present invention is an improvement in the treatment of migraine headaches. Although the present invention is not limited to any particular mechanism, by administering dihydroergotamine more efficiently or in a lower dose sublingually, major limitations of past treatments are circumvented thereby allowing for equal or better efficacy, significantly greater ease of administration and fewer side effects.

Although the present invention is not limited to any particular mechanism, migraines are believed to be caused by a rapid widening and narrowing of blood vessel walls in the brain and head. This causes the pain neurons in the blood vessel wall to become irritated. Blood vessels in the scalp are often involved. The following items and events (precipitant) have been reported to cause migraine attacks: hunger, cheese, changes in weather, nuts, fatigue, avocados, oral contraceptives, chocolate, menstrual periods, food cured with nitrates (e.g., hot dogs), emotional stress, meat tenderizers (e.g., MSG), and alcoholic beverages. It is not known why some individuals have migraines and others do not.

Migraines are classified as either a classical migraine or a common migraine. See, e.g., "Remington's Pharmaceutical Sciences", 17th ed., Mack Publishing Company (1985), p. 946 and Goodman and Gilman's "The Pharmaceutical Basis of Therapeutics", 8th ed., McGraw-Hill, Inc. (1990), pp. 944–947. A common migraine is much more likely to occur than a classical migraine. The classical migraine is associated with objective prodromal neurological signs and symptoms involving a headache that is preceded by a slowly expanding area of blindness surrounded by a sparkling edge that increases to involve up to one half of the field of vision of each eye. When the blindness clears up after approximately 20 minutes, it is often followed by a severe one-sided headache with nausea, vomiting and sensitivity to light. The common migraine is an attack without prodromal symptoms and begins as a slowly developing pain in the form of a headache that transforms into a mounting throbbing pain made worse by the slightest movement or noise. The pain is often on one side of the head only and usually occurs with nausea and sometimes vomiting.

The length of migraine is from about four hours to three days. Examples of causes of migraine are: stress related (e.g., anxiety, anger, worry, excitement, shock, depression), overexertion, changes of routine and changes of climate, food-related (e.g., chocolate, cheese and other dairy products, red wine, fried food and citrus fruits), sensory-related (e.g., bright lights or glare, loud noises and intense or penetrating smells), menstruation, contraceptive drugs and male or female age related hormonal changes.

Antimigraine drugs are well-known. See, e.g., U.S. Pat. Nos. 4,650,810, 4,914,125, 4,916,125, 4,994,483, 5,021,428, 5,200,413, 5,242,949, 5,248,684, 5,273,759, 5,317,103, 5,364,863, 5,399,574, 5,434,154, 5,441,969, 5,464,864, 5,466,699, 5,468,768, 5,491,148 and 5,494,910. Antimigraine drugs most commonly used in treatment of migraine fall into the following groups: beta-blocking agents, calcium channel blocking agents, antidepressants, selective 5-HT$_1$ agonists (sumatriptan), sedatives, local anesthetics, adrenergic blocking agents and mixtures of these.

The success of triptans in the treatment of migraine is limited. Such drugs (e.g., rizatriptan) show only a 60–70% efficacy.

Some antimigraine drugs may have direct, or indirect effect on the 5-hydroxytryptamine (5-HT) receptor system. The 5-HT receptor system is a potent intracranial vasoconstrictor. 5-HT receptors are presently delineated into three major subclassifications—5-HT$_1$, 5-HT$_2$, and 5-HT$_3$—each of which may also be heterogeneous. The receptor mediates vasoconstriction in the carotid vascular bed and thereby modifies blood flow therein. The various classes of compounds have been proposed as 5-HT agonists or antagonists for therapeutic use of migraine, but these have not always been specific to a particular type of 5-HT receptor.

Management of migraine is complicated by the lack of a single therapy which is effective in all patients with the same migraine type and by the need to select either an abortive or prophylactic method of treatment for these migraines. Further complications involves the current use of drugs that cause dependence with extended use. Another important consideration is that the more effective antimigraine agents in current use produce severe use-limiting side effects with long term usage.

Thus, there is a need for a safe and effective drug for the treatment of migraine and related disorders which can be used either prophylactically or to alleviate an established migraine that minimizes side effects preferably by allowing for the use of lower doses of the therapeutic compound.

DETAILED DESCRIPTION OF PREFERRED EMBODIMENTS

The present invention is directed, among other things, to methods of treating migraine by the sublingual administration of a migraine-ameliorating effective amount of dihydroergotamine or effective pharmaceutical salt thereof. While the precise mechanism by which the sublingual administration of a migraine-ameliorating effective amount of dihydroergotamine relieves migraine is unknown and without limiting the invention to any particular theory, it is believed that the treatment is effective because of its vasoconstrictive properties.

Sublingual administration is the preferred method of administration of the present invention. Although the present invention is not limited to any particular mechanism, it is believed that this method of administration allows for efficient transfer of the drug into the blood stream thereby maximizing the degree to which dihydroergotamine is absorbed for therapeutic intervention and minimizing the degree to which dihydroergotamine is absorbed orally. In other words, an advantage of such sublingual administration and the absorption of DHE through the sublingual mucosa is the effectiveness of lower doses of dihydroergotamine than intranasal dosing thereby, reducing any adverse effect. A further advantage for the sublingual route is the ease of administration.

Several pharmaceutically acceptable dosage forms of sublingual administration are well-known to those who are skilled in the art. The choice of the dosage form of sublingual administration method will be determined in part by the patient. The following dosage forms and methods of administration are merely exemplary and in no way limit the present invention.

Liquids can be used for the sublingual administration of DHE. Liquid formulations suitable for sublingual administration can consist of (a) solutions, such as a migraine-ameliorating effective amount of the agent dissolved in diluents such as water, or saline; (b) suspensions in an appropriate liquid; (c) suitable emulsions, all of which can be administered in suitable ways, including drops and sprays. These formulations may also contain excipients as are known in the art. Semi-solid formulations can may include gels, ointments and the like, containing, in addition to the active ingredient, such excipients as are known in the art. All of these formulations can be administered in suitable ways, including by spraying, dripping, painting or squirting under the tongue.

DHE, alone or in combination with other suitable components, can also be made into aerosol formulations to be administered via a spray. These aerosol formulations can be placed into pressurized acceptable propellants, such as dichlorodifluoromethane, nitrogen, and the like. They may also be formulated as pharmaceuticals for non-pressured preparations such as in a nebulizer or an atomizer.

In a preferred embodiment, DHE is administered sublingually in liquid form, most preferably in a flavored or unflavored physiological saline solution. In a preferred embodiment, the solution is administered as drops. In another preferred embodiment, DHE in liquid form is administered as a spray under the tongue.

In a preferred embodiment, DHE is administered as a solution comprising about 0.01% to about 0.5% DHE. More preferably, the solution is a physiological saline solution. In another embodiment, the DHE solution is an appropriate buffered mint flavored solution. Preferably, the amount of solution administered is about 0.1 ml (0.5 mg) to about 1 ml, depending on, for example, the concentration. More preferably, the amount of solution is about 0.25–0.5 ml.

In another preferred embodiment, the sublingual formulation of DHE comprises a hard or compressed powder tablet designed to dissolve under the tongue in about 30 to 120 seconds as disclosed in U.S. Pat. No. 6,221,392 to Khankari, et al., incorporated herein by reference. In another embodiment, the formulation of the hard tablet has a low grit component for an organoleptically pleasant mouth feel. The active component of the tablet is contained within a protective material. The particles are then added to a matrix comprising rapid dissolving, water soluble ingredients. In this regard, the present invention relates to a hard, compressed, rapidly dissolvable dosage form adapted for direct sublingual dosing. The dosage form includes an active ingredient and a matrix. The matrix is composed of at least a nondirect compression filler and a lubricant. The dosage form is adapted to rapidly dissolve under the tongue of a patient and thereby liberate the active ingredient. Preferably, the dosage form has a friability of about 2% or less when tested according to the U.S.P. The dosage form also preferably has a hardness of 15–50 Newtons (N).

The dosage forms described above are able to dissolve rapidly under the tongue of the patient, with a minimum of grit or other organoleptically unpleasant species. Moreover, because the dosage forms are hard and have low friability they can be handled and packaged like other, nonrapidly dissolving dosage forms.

Therefore, in another aspect of the present invention, there is provided a method of making a packaged, sublingually dissolvable dosage form. The method includes the steps of: (a) forming a mixture including an active ingredient (e.g., DHE) and a matrix including a nondirect compression filler and a lubricant; (b) compressing the mixture to form a plurality of hard, compressed, rapidly disintegrable dosage forms including the active ingredient distributed in the sublingually dissolvable matrix; and (c) storing the dosage forms in bulk prior to packaging. In a preferred particularly preferred embodiment, the dosage forms are then packaged in a lumen of a package such that there is more than one per package. Direct compression is the preferred method of forming the dosage forms. There is also provided hereby an openable and recloseable package containing a plurality of hard, compressed, rapidly dissolving tablets adapted for direct oral dosing as described above.

The protective materials used in accordance with the present invention may include any of the polymers conventionally utilized in the formation of microparticles, matrix-type microparticles and microcapsules. Among these are cellulosic materials such as naturally occurring cellulose and synthetic cellulose derivatives; acrylic polymers and vinyl polymers. Other simple polymers include proteinaceous materials such as gelatin, polypeptides and natural and synthetic shellacs and waxes. Protective polymers may also include ethylcellulose, methylcellulose, carboxymethyl cellulose and acrylic resin material sold under the registered trademark EUDRAGIT by Rhone Pharma GmbH of Weiterstadt, Germany.

In another preferred embodiment, the present invention comprises an effervescent agent. The effervescent agent is provided in an amount of between about 5% and about 95% by weight, based on the weight of the finished tablet, and more preferably in an amount of between about 30% and about 80% by weight. It is particularly preferred that sufficient effervescent material be provided such that the evolved gas is more than about 5 cm$^3$ but less that about 30 cm$^3$, upon exposure of the tablet to an aqueous environment. Sublingual compositions comprising effervescent agents are provided in Pather U.S. Pat. No. 6,200,604 which is incorporated herein by reference.

In one embodiment, the effervescent agent(s) of the present invention evolve carbon dioxide. Although not limited to a particular mechanism, this reaction is most often the result of the reaction of a soluble acid source and a source of carbon dioxide such as an alkaline carbonate or bicarbonate. The effervescent agent(s) of the present invention is not always based upon a reaction which forms carbon dioxide. The acid sources may be any which are safe for human consumption and may generally include food acids, acid and hydrite antacids such as, for example: citric acid, tartaric, amalic, fumeric, adipic and succinics. Carbonate sources include dry solid carbonate and bicarbonate salt such as, preferably, sodium bicarbonate, sodium carbonate, potassium bicarbonate and potassium carbonate, magnesium carbonate and the like. Reactants which evolve oxygen or other gasses which are safe for human consumption are also considered within the scope of the present invention.

The dosage forms of the present invention may also include a pH adjusting substance. Although the present invention is not limited to any particular mechanism, the pH of aqueous environments can influence the relative concentration of the ionized and unionized forms of the drug present in solution. The pH of the local environment, e.g., saliva in immediate contact with the tablet and any drug that may have dissolved from it, may be adjusted by incorporating in the tablet pH adjusting substances which permit the relative portions of the ionized and unionized forms of the drug to be controlled. In the present invention it is contemplated that the pH of the micro-environment will be altered such that the DHE mesylate salt will exist as the DHE base.

Suitable pH adjusting agents for use in the present invention include, but are not limited to weak acids or bases in amounts additional to that required for the effervescence or, preferably, any buffer system that is not harmful to the oral mucosa. Suitable pH adjusting substance for use in the present invention include, but are not limited to, any of the acids or bases previously mentioned as effervescent compounds, disodium hydrogen phosphate, sodium dihydrogen phosphate and the equivalent potassium salt.

The dose administered in the context of the present invention should be a migraine-ameliorating effective amount of DHE. Current modes of administration of DHE for migraine (e.g., oral and nasal administration) necessitate higher doses of DHE to be used than parenteral administration. Higher doses may cause adverse side effects in the patient. Nausea and vomiting are a common side effects. More severe side effects include stoke, heart palpitations and, rarely, death. One way to reduce the severity of side effects would be to lower the dose of DHE administered to the patient while still maintaining a therapeutic level of DHE at the target site. A sublingual formulation of DHE would permit the use of lower doses of DHE since a greater portion of the medication would be absorbed directly into the blood stream thereby allowing a direct route to the afflicted target area. For example, as compared to the current marketed nasal spray formulation, the present invention contemplates about a 25% reduction in dose, giving a preferred dose of about 1.5 mg. In a more preferred embodiment, as compared to the current marketed nasal spray formulation, the present invention contemplates about a 50% reduction in dose, giving a preferred dose of about 1.0 mg, which is the same dose as parenteral administration In yet a more preferred embodiment, the present invention contemplates about a 75% in dose as compared to the current marketed nasal spray formulation, giving a preferred dose of about 0.5 mg. In yet another embodiment, the present invention contemplates a sublingual dose that delivers about efficacy equivalent to intranasal administration. Sublingual formulations of DHE will also allow for ease of administration by the patient as compared to available modes of administration.

Preferably, the symptoms of the migraine are relieved within about 10 to about 120 minutes after administration of a sublingual dose of DHE, and more typically within about 10 to about 30 minutes, and if they are not relieved within about 120 minutes, a second dose can be administered, as also recommended for the parenteral administration.

The methods of the invention further include a method of treatment of migraine comprising the sublingual administration of DHE, in combination with the administration of at least one anti-inflammatory compound. Anti-inflammatory compounds include steroids, particularly glucocorticoids, for example, cortisol, cortisone, prednisolone, dexamethasone and the like; and nonsteroids, particularly salicylates (such as aspirin), pyrazolon derivatives (such as phenylbutazone), indomethacin and sulindac, fenamates, and propionic acid derivatives (such as ibuprofen). In a preferred embodiment, the nonsteroidal anti-inflammatory agent ketorolac tromethamine or diclofenac is administered.

The methods of the invention further include a method of treatment of migraine comprising the sublingual administration of DHE, in combination with the administration of at least one antiemetic compound. As the mechanism of action of many antiemetics is not fully understood, the selection of the antiemetic is based on empirical reasoning. Antiemetics fall into the following groups: sedatives and hypnotics (barbiturates), anticholinergic agents (scopolamine), antihistamines (dimenhydrinate and many others), phenothiazines (chlorpromazine, prochloroperazine, fluphenazine, triethylperazine) and miscellaneous agents (diphenidole, cyclizine, metoclopramide, trimethobenzamide, benzquinamide, etc. In a preferred embodiment, the antiemetic agent meclizine or metoclopramide or prochloroperazine is also administered by the sublingual or buccal route.

The methods of the invention further include a method of treatment of migraine comprising the sublingual administration of DHE in combination with the administration of at least one non-DHE antimigraine drug, such as pizotifen, propranolol, valproate, amitriptyline, methylsergide, sumatriptan or other triptans and flunarizine.

The present invention is not limited in the method in which DHE is administered in combination with other pharmacological agents. For example, the other pharmacological agents may be administered concurrently or sequentially with DHE. Likewise, the other pharmacological agents may be administered by modes of administration other that sublingually. For example, they may be administered orally, buccally, intravenously, subcutaneously, nasally or via the rectum. Additionally, they may be administered in fast release, slow release or controlled release formulations.

The embodiment of the present invention utilizing bio/mucoadhesive agents is contemplated for use in the administration of DHE and its pharmacologically acceptable salts. The particles of DHE or salt thereof will suitably have, for example, a maximum particle size of about 50 $\mu$m but will preferably not be greater than about 10–25 $\mu$m. DHE is caused to adhere to the carrier particles by dry mixing of the ingredients during a period of time of sufficient length. This time period can vary according to the mixing equipment used. A person skilled in the art will have no difficulty in determining by experimentation a suitable mixing time for a given combination of active substance, bio/mucoadhesion promoting agent and carrier with a particular brand or model of mixing equipment.

In another embodiment, the present invention contemplates the incorporation of a disintegrating agent in the composition of the invention. Such an agent which will accelerate the dispersion of the carrier particles. Examples of disintegrating agents according to the invention include cross-linked polyvinylpyrrolidone, carboxymethyl starch, natural starch, microcrystalline cellulose, cellulose gum and mixtures of these. In a preferred embodiment of the present invention, the preferred content of disintegrating agent is from 0.1% to 25% of the composition. In a more preferred embodiment, the preferred percentage of the disintegrating agent is between 1.0% and 10% of the composition. As can be seen, the amounts of the disintegrating agent and the bio/mucoadhesion promoting agent that may be used overlap somewhat, and, in some embodiments, it may be preferred that both functions are served by the same substance. However, it is important to note that these two categories of excipients are not equivalent, and there are efficiently functioning disintegrants which do not possess bio/mucoadhesive properties, and vice versa.

The ordered mixtures prepared in embodiments of the present invention can be incorporated into various kinds of pharmaceutical preparations intended for sublingual administration. Irrespective of the form given to the preparation, it is important that the preparation is essentially free from water, since its bio/mucoadhesion promoting character results from its practically instantaneous hydration when brought into contact with water or saliva. Premature hydration would drastically decrease the mucoadhesion promoting properties and result in a premature dissolution of the active substance.

In embodiments of the present invention, a pharmaceutical composition for the preferred sublingual route of administration can be obtained by combining an aforementioned ordered mixture with conventional pharmaceutical additives and excipients used in the art for sublingual preparations. Appropriate formulation methods are well known to the person skilled in the art; see, for instance, Pharmaceutical Dosage Forms: Tablets. Volume 1. 2nd Edition, Lieberman H A, et al.: Eds.: Marcel Dekker, New York and Basel 1989, p. 354–356, and literature cited therein, all of which are incorporated herein by reference. Suitable additives comprise, for example, additional carrier agents, preservatives, lubricants, gliding agents, disintegrants, flavorings, and dyestuffs.

Thus, in certain embodiments, the invention provides a dosage form which is easy and inexpensive to manufacture, enables rapid active substance release, promotes a rapid uptake of the active agent or agents through the oral mucosa, and enhances the uptake of otherwise poorly soluble substances, such as peptides.

EXAMPLES

The following examples serve to illustrate certain preferred embodiments and aspects of the present invention and are not to be construed as limiting the scope thereof.

In the experimental disclosure which follows, the following abbreviations apply: eq (equivalents); M (Molar); $\mu$M (micromolar); N (Normal); mol (moles); mmol (millimoles); $\mu$mol (micromoles); nmol (nanomoles); g (grams); mg (milligrams); $\mu$g (micrograms); L (liters); ml (milliliters); $\mu$l (microliters); cm (centimeters); mm (millimeters); $\mu$m (micrometers); nm (nanometers); ° C. (degrees Centigrade); n (number); Novartis (CH-4002 Basel, Switzerland).

Example 1

This example illustrates a method of administering a migraine-ameliorating amount of DHE sublingually.

A dose of a DHE sublingual compound is placed by the patient or medical professional under the tongue. The compound is allowed to dissolve fully. If the symptoms are not relieved within 30 to 60 minutes, a second dose is administered.

Example 2

This example illustrates a method of administering a migraine-ameliorating amount of DHE sublingually.

This experiment utilizes two test groups of patients. All of the patients are suffering from migraines. One group receives a 1 mg dose of sublingual DHE, the other group receives a placebo. The DHE sublingual formulation is placed by the patients or medical professional under the tongue. The DHE sublingual formulation is allowed to dissolve fully. If the symptoms are not relieved within 20 to 40 minutes, a second dose is administered. Results are compared between the test group and the placebo group. The results show greater amelioration of migraine symptoms in the test group as compared to the placebo control group. The difference in amelioration of migraine symptoms are statistically significant.

Example 3

This example compares the effect on migraine of subcutaneous injection vs. the sublingual administration of the present invention.

This experiment utilizes three test groups of patients. All of the patients are suffering from migraines. One group receives a 1 mg dose of sublingual DHE tablet and a placebo subcutaneous injection, the second group receives a 1 mg subcutaneous injection of a pharmaceutical formulation comprising DHE and a placebo sublingual tablet, and the third group receives a placebo subcutaneous injection and a placebo sublingual tablet. Results are compared between the active sublingual test group and the active subcutaneous test group. The results show equivalent amelioration of migraine symptoms between the two active groups indicating that the easier sublingual administration of the present invention is as effective as the more difficult subcutaneous administration of DHE. Additionally, the results show the effectiveness of DHE administered sublingually or subcutaneously in treating migraine as compared to the respective placebo.

Example 4

This example compares the effect on migraine of nasal administration of DHE vs. the sublingual administration of the present invention.

This experiment utilizes three test groups of patients. All of the patients are suffering from migraines. One group receives a 2 mg dose of sublingual DHE and placebo intranasal spray, the second group receives a 2 mg nasally administered dose of a pharmaceutical formulation comprising DHE and a placebo sublingual tablet, the third group receives a placebo sublingual tablet and a placebo intranasal spray. Results are compared between the active sublingual test group and the active nasal test group. The results show equivalent amelioration of migraine symptoms between the two groups indicating that the sublingual administration of the present invention is as effective as the nasal administration of DHE. Additionally, the results show the effectiveness of DHE in treating migraine as compared to the respective placebo.

Example 5

This example evaluates the uptake in sublingual vs. subcutaneous administration of DHE.

In this experiment one patient suffering from migraine pain is administered a migraine ameliorating dose of DHE as a sublingual tablet formulated as described in Example 1. The plasma concentration of DHE is monitored for a time of 24 hours after the administration. It is demonstrated that the uptake of DHE is rapid, with the maximum value attained after about 30–60 minutes. The rate and amount of DHE in the plasma is compared to that obtained by subcutaneous administration. This shows that a sublingual preparation according to the invention gives a similar rapid uptake of the active agent as the subcutaneous rout of administration.

Example 6

This example shows the results of a two-way crossover design study in 12 non-smoking healthy normal volunteers. Each volunteer is administered DHE sublingual tablet manufactured as defined in this patent. In one treatment the tablet is administered under the tongue and in the crossover treatment the subject is administered the tablet orally with about 240 ml of water. Blood samples are taken serially over a 24 hour duration post administration and assayed for unchanged DHE and the principle 8-hydroxy DHE metabolite. The results show that the when the tablet is administered sublingually the levels of the active DHE are at least 200% higher than when given orally. The orally administered treatment gives levels that are principally the inactive 8-hydroxymetabilite. These results show that minimal oral absorption occurs with sublingual tablet when formulated as defined in this patent.

Example 7

In this example the intrinsic permeability of DHE was shown after it was sublingually administered DHE in a Cynomogolius monkey.

The test DHE was obtained from as DHE 45® Injection, USP (manufactured by Novartis). Specific information follows.

| Test Article | DHE 45 ® |
|---|---|
| Lot No. | 551 (expires November 2002) |
| Concentration | 1.0 mg/mL |
| Storage Conditions | Room temperature |

Prior to dose administration, the animal was restrained and anesthetized with an appropriate amount of ketamine. Using a calibrated pipette, 0.5 mL of dosing solution was placed under the animal's tongue immediately after swabbing excess saliva with a gauze pad (the gauze pad will be discarded). The animal's head was restrained for approximately 5 minutes in such a manner to minimize any loss of the dose solution through the animal's mouth or down the animal's throat.

Mortality and moribundity checks were done twice daily (a.m. and p.m.). Cageside observation for general health and appearance was done once daily. No unusual observations were noted throughout the duration of the study.

Blood (approximately 1 mL) was collected from each animal prior to dosing (predose) and at 0.1, 0.2, 0.3, 0.4, 0.5, 1, 2, 4, 8, and 12 hours postdose. Blood was collected via a femoral vein into sodium-heparinized tubes.

Blood was maintained on wet ice, in chilled Kryoracks, or at approximately 5° C. prior to centrifugation to obtain plasma. Centrifugation was begin within 30 minutes of collection. The blood samples were centrifuged at approximately 5° C. for approximately 10 minutes at approximately 4,000 rpm. Plasma was harvested and stored on dry ice or at approximately −70° C. prior to shipment.

The plasma was assayed for DHE using standard techniques. Test data is presented in Tables 1 and 2 below. Table 1 shows the plasma concentration of DHE at various time points after administration. Table 2 shows the AUCt (tissue concentration vs time curve), Cmax (maximum concentration), Tmax (time point of maximum concentration) and t½ (half life) of the DHE in the plasma. The results showed that the sublingual administration of DHE resulted in the rapid detection of DHE in the blood plasma.

TABLE 1

| | Time | DHE |
|---|---|---|
| 1 | 0.0 (hours) | 0.0 (pg/ml) |
| 2 | .1 | 8258.3 |
| 3 | .2 | 6952.8 |
| 4 | .2 | 3922.6 |
| 5 | .5 | 2335.9 |
| 6 | 1.0 | 1141.9 |
| 7 | 2.0 | 710.9 |
| 8 | 4.0 | 343.4 |
| 9 | 8.0 | 75.7 |
| 10 | 12.0 | 39 |

TABLE 2

| AUC (t) | Cmax | Tmax | t½ |
|---|---|---|---|
| 6133 | 8258 | 5 min | 2.2 h |

Example 7

This example presents a liquid formulation of DHE that will be applied as a sublingual spray.

| | |
|---|---|
| Dihydroergotamine mesylate | 250 mg |
| Methyl-β-cyclodextrin D.S. 1.8 | 2.5 g |
| Benzalkonium Chloride | 0.01% |
| Sodium EDTA | 0.05–0.1% |
| Sorbitol | 5% |
| Purified water to | 100 ml |
| 100 μl = 250 μg DHE mesylate | |

Example 8

This example presents a sol-gel formulation of DHE that will be applied as a sublingual spray.

| | |
|---|---|
| Dihydroergotamine mesylate | 0.5 g |
| Methyl-β-cyclodextrin D.S. 1.8 | 5 g |
| Benzalkonium Chloride | 0.01% |
| Sodium EDTA | 0.05–0.1% |
| Sorbitol | 5% |
| Hydroxypropylmethylcellulose | 1–2% |
| Purified water to | 100 ml |
| 100 μl gel = 500 μg DHE | |

Example 9

This example presents a powder formulation of DHE that will be applied as a sublingual aerosol.

| | |
|---|---|
| Dihydroergotamine mesylate | 0.5 mg |
| Methyl-β-cyclodextrin | 5 mg |
| Mannitol | 4.5 mg |
| 10 mg powder = 500 μg DHE mesylate | |

Example 10

This example presents another powder formulation of DHE that will be applied as a sublingual aerosol.

| | |
|---|---|
| Dihydroergotamine mesylate | 0.5 mg |
| Dextran (average M.W. 70.000) | 9.5 mg |
| 10 mg powder= 500 μg DHE mesylate | |

Example 11

This example presents another powder formulation of DHE that will be applied as a sublingual aerosol.

| | |
|---|---|
| Dihydroergotamine mesylate | 0.5 mg |
| β-cyclodextrin | 5 mg |
| Lactose | 4.5 mg |
| 10 mg powder = 500 μg DHE mesylate | |

As is evident from the foregoing, the present invention contemplates novel treatment methods for migraines comprising the sublingual administration of dihydroergotamine. These novel methods allow for the circumvention of major limitations of past treatments thereby allowing for higher efficacy and fewer side effects of treatment at lower doses.

I claim:

1. A method of treating migraine comprising: the application of a spray to the sublingual mucosa of a patient wherein said spray consists of one active ingredient and one or more inactive ingredients, wherein said active ingredient is dihydroergotamine and wherein at least one of said one or more inactive inactive ingredients is selected from the group consisting of cyclodextrins, dextrans, sugar alcohols and mixtures thereof.

2. A pharmaceutical composition according to claim 1, wherein said dextrans have average molecular weight between about 10,000 and about 100,000.

3. A method of treating migraine comprising: the application of an aerosol to the sublingual mucosa of a patient wherein said aerosol consists of one active ingredient and one or more inactive ingredients, wherein said active ingredient is dihydroergotamine and wherein at least one or said one or more inactive ingredients is selected from the group consisting of cyclodextrins, dextrans, sugar alcohols and mixtures thereof.

\* \* \* \* \*